US011304961B2

(12) United States Patent
Kreyenborg et al.

(10) Patent No.: US 11,304,961 B2
(45) Date of Patent: *Apr. 19, 2022

(54) COMPOSITIONS COMPRISING DEXAMETHASONE

(71) Applicant: Dexcel Pharma Technologies Ltd., Or-Akiva (IL)

(72) Inventors: Caterina Kreyenborg, Münster (DE); Elisabeth Meimberg, Emsdetten (DE); Corinna Tissen, Senden (DE); Karl-Heinz Bannefeld, Münster (DE); Tomer Gold, Herzliya (IL)

(73) Assignee: DEXCEL PHARMA TECHNOLOGIES LTD., Or-Akiva (IL)

(*) Notice: Subject to any disclaimer, the term of this patent is extended or adjusted under 35 U.S.C. 154(b) by 0 days.

This patent is subject to a terminal disclaimer.

(21) Appl. No.: 16/743,136

(22) Filed: Jan. 15, 2020

(65) Prior Publication Data

US 2020/0147106 A1  May 14, 2020

Related U.S. Application Data

(63) Continuation of application No. 15/845,232, filed on Dec. 18, 2017, now Pat. No. 10,537,585.

(51) Int. Cl.
*A61K 31/573* (2006.01)
*A61K 9/20* (2006.01)
*A61K 31/454* (2006.01)
*A61K 9/00* (2006.01)
*A61P 7/00* (2006.01)
*A61K 9/16* (2006.01)

(52) U.S. Cl.
CPC .......... *A61K 31/573* (2013.01); *A61K 9/0053* (2013.01); *A61K 9/1694* (2013.01); *A61K 9/2013* (2013.01); *A61K 9/2018* (2013.01); *A61K 9/2027* (2013.01); *A61K 9/2059* (2013.01); *A61K 31/454* (2013.01); *A61P 7/00* (2018.01)

(58) Field of Classification Search
CPC combination set(s) only.
See application file for complete search history.

(56) References Cited

U.S. PATENT DOCUMENTS

| | | | |
|---|---|---|---|
| 3,231,468 A | 1/1966 | Macek et al. | |
| 5,593,990 A | 1/1997 | D'Amato | |
| 5,635,517 A | 6/1997 | Muller et al. | |
| 5,643,915 A | 7/1997 | Andrulis, Jr. et al. | |
| 5,707,634 A | 1/1998 | Schmitt | |
| 5,780,454 A | 7/1998 | Adams et al. | |
| 5,811,547 A | 9/1998 | Nakamichi et al. | |
| 6,045,501 A | 4/2000 | Elsayed et al. | |
| 6,087,350 A | 7/2000 | Johnson et al. | |
| 6,090,794 A | 7/2000 | Martuza et al. | |
| 6,315,720 B1 | 11/2001 | Williams et al. | |
| 6,316,471 B1 | 11/2001 | Muller et al. | |
| 6,503,537 B2 | 1/2003 | Yang | |
| 6,552,065 B2 | 4/2003 | Remiszewski et al. | |
| 6,561,977 B2 | 5/2003 | Williams et al. | |
| 6,592,901 B2 | 7/2003 | Durig et al. | |
| 6,713,446 B2 | 3/2004 | Gupta | |
| 7,101,884 B2 | 9/2006 | Arrington et al. | |
| 7,189,740 B2 | 3/2007 | Zeldis | |
| 7,230,012 B2 | 6/2007 | D'Angio et al. | |
| 7,232,818 B2 | 6/2007 | Smyth et al. | |
| 7,325,355 B2 | 2/2008 | Zeldis | |
| 7,435,745 B2 | 10/2008 | D'Amato | |
| 7,442,830 B1 | 10/2008 | Olhava et al. | |
| 7,479,499 B2 | 1/2009 | Govindarajan et al. | |
| 7,687,456 B2 | 3/2010 | Zhou et al. | |
| 7,736,673 B2 | 6/2010 | Heaton et al. | |
| 7,737,112 B2 | 6/2010 | Lewis et al. | |
| 7,842,293 B2 | 11/2010 | Afar | |
| 7,989,494 B2 | 8/2011 | Acemoglu et al. | |
| 7,989,639 B2 | 8/2011 | Bajwa et al. | |
| 8,093,220 B2 | 1/2012 | Atadja | |
| 8,198,262 B2 | 6/2012 | Zeldis | |
| 8,435,992 B2 | 5/2013 | Ocio et al. | |
| 8,546,608 B2 | 10/2013 | Bernardini et al. | |
| 8,563,700 B2 | 10/2013 | Lutz et al. | |
| 8,575,216 B2 | 11/2013 | Strair | |
| 8,632,772 B2 | 1/2014 | Anderson et al. | |
| 8,633,179 B2 | 1/2014 | Ferrando et al. | |
| 8,741,929 B2 | 6/2014 | Zeldis | |

(Continued)

FOREIGN PATENT DOCUMENTS

WO   WO 93/09763    *  5/1993
WO   WO 2005046686 A1   5/2005

(Continued)

OTHER PUBLICATIONS

Dexamethasone tablet (Package Leaflet: Information for the User, 2010) (hereinafter Dexamethasone II) (already of record, but a clear copy).*
Dexamethasone tablet (Package leaflet: Information for the Patient, 2010, pp. 1-3).
Dexamethasone tablet (Package Leaflet: Information for the User, 2010) (hereinafter Dexamethasone 11).
Sodium carboxyl methylstarch (Chemical Look, Sodium carboxyl methylstarch, 2016, pp. 1-2).
Dexamethasone 20 mg tablets, KRKA, Package leaflet, retrieved from https://www.drugs.com/uk/dexamethasone-20-mg-tablets-leaflet.html Jul. 15, 2016 (Jul. 15, 2016), 2 pgs.
Dexamethasone 0.5 mg, 2 mg, Rekah Pharmaceutical Prod. Ltd., Package leaflet, retrieved from https://www.old.health.gov.il/units/pharmacy/trufot/alonim/Rishum_1_258926016.pdf Mar. 31, 2014 (Mar. 31, 2014), 1 pg.

(Continued)

*Primary Examiner* — Kathrien A Cruz
(74) *Attorney, Agent, or Firm* — Rothwell, Figg, Ernst & Manbeck, P.C.

(57) ABSTRACT

A pharmaceutical composition useful for the treatment of multiple myeloma in combination with an anti-cancer drug is provided. The pharmaceutical composition includes high-dose dexamethasone or a pharmaceutically acceptable salt or solvate thereof.

28 Claims, No Drawings

(56) References Cited

U.S. PATENT DOCUMENTS

| | | |
|---|---|---|
| 8,822,438 B2 | 9/2014 | Auerbach et al. |
| 8,828,427 B2 | 9/2014 | Tutino et al. |
| 8,858,993 B2 | 10/2014 | Gold et al. |
| 8,859,504 B2 | 10/2014 | Elliott et al. |
| 8,883,842 B2 | 11/2014 | Atadja |
| 8,901,110 B2 | 12/2014 | Kim et al. |
| 8,940,705 B2 | 1/2015 | Diamond et al. |
| 9,066,977 B2 | 6/2015 | Aikawa et al. |
| 9,101,621 B2 | 8/2015 | Zeldis |
| 9,175,081 B2 | 11/2015 | Williams et al. |
| 9,192,665 B2 | 11/2015 | Zugmaier et al. |
| 9,220,716 B2 | 12/2015 | Bischoff et al. |
| 9,492,434 B2 | 11/2016 | Luesch et al. |
| 9,493,582 B2 | 11/2016 | Antle et al. |
| 9,504,656 B2 | 11/2016 | Vamvakas et al. |
| 9,511,109 B2 | 12/2016 | Kirk et al. |
| 2002/0055495 A1 | 5/2002 | Anthony |
| 2002/0085978 A1 | 7/2002 | Buenafe et al. |
| 2003/0021841 A1 | 1/2003 | Matharu et al. |
| 2003/0166598 A1 | 9/2003 | Decaudin et al. |
| 2004/0054104 A1 | 3/2004 | Pacetti |
| 2004/0266809 A1 | 12/2004 | Emanuel et al. |
| 2005/0053655 A1 | 3/2005 | Yang et al. |
| 2005/0148524 A1 | 7/2005 | Zeldis et al. |
| 2006/0034915 A1 | 2/2006 | Rice et al. |
| 2007/0134312 A1 | 6/2007 | Hussein |
| 2007/0178051 A1 | 8/2007 | Pruitt et al. |
| 2007/0208057 A1 | 9/2007 | Zeldis |
| 2008/0095845 A1 | 4/2008 | Luber et al. |
| 2008/0233155 A1 | 9/2008 | Moingeon et al. |
| 2008/0305150 A1 | 12/2008 | Chen et al. |
| 2008/0305166 A1 | 12/2008 | Durig |
| 2008/0305176 A1 | 12/2008 | Lewis et al. |
| 2009/0004262 A1 | 1/2009 | Shaw et al. |
| 2009/0029901 A1 | 1/2009 | Wood-Kaczmar |
| 2009/0035375 A1 | 2/2009 | Skrtic et al. |
| 2009/0074824 A1 | 3/2009 | Vila Pena et al. |
| 2009/0263476 A1 | 10/2009 | Jobdevairakkam et al. |
| 2010/0216755 A1 | 8/2010 | Nihei et al. |
| 2010/0286090 A1 | 11/2010 | Mitsiades et al. |
| 2011/0021470 A1 | 1/2011 | Auerbach et al. |
| 2011/0280849 A1 | 11/2011 | Zhang et al. |
| 2012/0107417 A1 | 5/2012 | Takahashi et al. |
| 2012/0251496 A1 | 10/2012 | Wick |
| 2012/0258940 A1 | 10/2012 | Caponigro et al. |
| 2012/0269802 A1 | 10/2012 | Shaughnessy, Jr. et al. |
| 2012/0288554 A1 | 11/2012 | Brown |
| 2012/0289488 A1 | 11/2012 | Bond et al. |
| 2012/0309704 A1 | 12/2012 | Arcangeli et al. |
| 2013/0287774 A1 | 10/2013 | Zugmaier et al. |
| 2013/0310352 A1 | 11/2013 | Yi et al. |
| 2013/0344116 A1 | 12/2013 | Wong et al. |
| 2014/0051662 A1 | 2/2014 | Moussy et al. |
| 2014/0161819 A1 | 6/2014 | Hann et al. |
| 2014/0274947 A1 | 9/2014 | Crawford et al. |
| 2014/0348823 A1 | 11/2014 | Lichenstein et al. |
| 2015/0051163 A1 | 2/2015 | Keilhack et al. |
| 2015/0140000 A1 | 5/2015 | Bonnafous et al. |
| 2015/0231096 A1 | 8/2015 | Lichenstein et al. |
| 2015/0250873 A1 | 9/2015 | Kerschbaumer et al. |
| 2015/0272970 A1 | 10/2015 | Cordon-Cardo et al. |
| 2016/0002330 A1 | 1/2016 | Meade |
| 2016/0045483 A1 | 2/2016 | Stahly et al. |
| 2016/0377621 A1 | 12/2016 | Yarchoan et al. |

FOREIGN PATENT DOCUMENTS

| | | | |
|---|---|---|---|
| WO | WO 2010119300 A2 | | 10/2010 |
| WO | WO 2016/198166 | * | 12/2016 |
| WO | WO 2017058754 A1 | | 4/2017 |
| WO | WO 2017079572 A1 | | 5/2017 |
| WO | WO 2017140743 A1 | | 8/2017 |

OTHER PUBLICATIONS

Weber et al.: "Thalidomide alone or with dexamethasone for previously untreated multiple myeloma." J. Clin. Oncol., vol. 21, No. 1, pp. 16-19 Jan. 31, 2003 (Jan. 31, 2003).

"Handbook of Pharmaceutical Excipients (5 Ed.)", edited by Rowe R.C. et al.,pp. 389, 430, 611, 701, 725 Dec. 31, 2006 (Dec. 31, 2006).

Anagostopoulos et al., "Thaidomide and dexamethasone for resistant multiple myeloma", British Journal of Haematology, 2003, 121, 768-771.

Liberman et al., "Pharmaceutical dosage forms: Tablets" vol. 1, Chapter 3 Dec. 31, 1989 (Dec. 31, 1989), 65 pgs.

International Search Report and Written Opinion cited in PCT/IL2018/051361, dated Mar. 19, 2019, 11 pages.

Kandela et al., Study of tablet-coating parameters for a pan coater through video imaging and Monte Carlo simulation, Powder Technology • Dec. 2010, 11 pages.

Dexamethasone II 20 mg tablets Dexamethasone 40 mg tablets, Package Leaflet: Information for the User, Consilient Health (UK) Limited, Jul. 2016, 2 pages.

* cited by examiner

COMPOSITIONS COMPRISING DEXAMETHASONE

CROSS REFERENCE TO RELATED APPLICATION

This application is a continuation of U.S. patent application Ser. No. 15/845,232 filed on Dec. 18, 2017, the disclosures of which is incorporated herein in its entirety by reference.

TECHNICAL FIELD

Compositions comprising dexamethasone, methods of preparation and use thereof are provided.

BACKGROUND

Dexamethasone is a corticosteroid used in a variety of conditions including allergic disorders, skin conditions, ulcerative colitis, arthritis, lupus, psoriasis, and breathing disorders. It is also used as a direct chemotherapeutic agent in certain haematological malignancies, especially in the treatment of multiple myeloma, in which dexamethasone is given in combination with other chemotherapeutic drugs including, in particular, thalidomide.

U.S. Pat. No. 9,504,656 discloses an oral pharmaceutical composition comprising a matrix fill comprising: at least one solubility enhancing agent; at least one viscosity enhancing agent; at least one surfactant; at least one pH modifying agent; water; and at least one active pharmaceutical ingredient dissolved in the matrix fill; wherein the matrix fill comprises a single phase liquid that is encapsulated in a soft capsule shell.

U.S. 2006/0034915 discloses a tablet comprising an amount of from 2 to 0.02% w/w of the formulation of dexamethasone and from 0.5% to 5% w/w of the formulation of a viscosity increasing excipient and a process of manufacturing same.

U.S. 2002/0085978 discloses a pharmaceutical composition comprising a glucocorticosteroid, a propellant, a cosolvent, and a radical quencher.

There remains an unmet need for compositions comprising dexamethasone containing high-load of the active pharmaceutical ingredient.

BRIEF SUMMARY

There is provided a pharmaceutical composition comprising dexamethasone or a pharmaceutically acceptable salt or solvate thereof as an active pharmaceutical ingredient in an amount of from about 15 to about 25 weight percent, the pharmaceutical composition further comprising a filler, a binder, a disintegrant and a lubricant.

The pharmaceutical composition provides high-load of dexamethasone for oral administration in a single dose thereby allowing improved compliance to recommended dosing regimens in patients in need thereof.

In a first aspect, there is provided a pharmaceutical composition comprising:
i) about 15 to about 25 wt.-% dexamethasone or a pharmaceutically acceptable salt or solvate thereof;
ii) about 45 to about 60 wt.-% filler;
iii) about 10 to about 30 wt.-% binder;
iv) about 2 to about 10 wt.-% disintegrant; and
v) about 0.01 to about 5 wt.-% lubricant;
wherein presence of all components add to 100 wt.-%.

In one embodiment, the filler comprises lactose.

In another embodiment, the binder comprises starch, polyvinylpyrrolidone or a combination thereof.

In yet another embodiment, the disintegrant comprises sodium carboxymethyl starch.

In other embodiments, the lubricant comprises magnesium stearate.

In some embodiment, the pharmaceutical composition is in the form of a tablet.

In particular embodiments, the pharmaceutical composition is in the form of an uncoated tablet.

In various embodiments, the pharmaceutical composition is formulated into a unit dosage form suitable for oral administration. In one embodiment, the unit dosage form comprises from 15 to 25 mg of dexamethasone or a pharmaceutically acceptable salt or solvate thereof. In specific embodiments, the unit dosage form comprises 20 mg of dexamethasone.

In another embodiment, there is provided a process for preparing the pharmaceutical composition disclosed herein, the process comprising:
i) wet granulating dexamethasone or a pharmaceutically acceptable salt or solvate thereof, a binder, a filler, and a disintegrant to obtain a wet granulate;
ii) drying the wet granulate of step (i) to obtain a dry granulate having a Loss on Drying (LOD) % of about 1.5% to about 5%; and
iii) admixing the dry granulate of step (ii) with a lubricant.

In certain embodiments, the step of wet granulating dexamethasone or a pharmaceutically acceptable salt or solvate thereof, a binder, a filler, and a disintegrant comprises $i_a$) dry mixing dexamethasone or a pharmaceutically acceptable salt or solvate thereof, a binder, a filler, and a disintegrant to obtain a dry mixture; and $i_b$) wetting the thus obtained dry mixture with a granulation solution or suspension to obtain a wet granulate.

In some embodiments, the granulation solution or suspension comprises aqueous medium. In several embodiments, the granulation solution or suspension further comprises a binder.

In other embodiments, the process further comprises a step prior to step (iii), the step comprising admixing the dry granulate of step (ii) with a disintegrant which may be the same or different as the disintegrant in step (i), with each possibility representing a separate embodiment.

In further embodiments, the process further comprises the step of iv) compressing the pharmaceutical composition of step iii) to obtain a tablet or a caplet.

In various embodiments, the pharmaceutical composition described herein is useful for the treatment of multiple myeloma in combination with an anti-cancer drug.

In one embodiment, the anti-cancer drug is thalidomide. In some embodiments, the pharmaceutical composition disclosed herein and the anti-cancer drug are administered simultaneously, separately or sequentially. Each possibility represents a separate embodiment.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION

As disclosed herein, there is provided an oral pharmaceutical composition, preferably in the form of an uncoated tablet, the composition containing high-load of dexamethasone or a pharmaceutically acceptable salt or solvate thereof.

Advantageously, the composition comprises from about 15 to about 25 w/w dexamethasone or a pharmaceutically acceptable salt or solvate thereof thereby providing a unit dosage form containing 20 mg dexamethasone. The composition affords significantly high loading of the active ingredient. As the recommended dose of dexamethasone for treatment of multiple myeloma is typically 20 or 40 mg/day, improved compliance to recommended dosing regimens is afforded by the composition disclosed herein.

According to certain aspects and embodiments, there is provided a pharmaceutical composition comprising dexamethasone or a pharmaceutically acceptable salt or solvate thereof in an amount of from about 15 to about 25% w/w, a filler in an amount of from about 45 to about 60% w/w, a binder in an amount of from about 10 to about 30% w/w; a disintegrant in an amount of from about 2 to about 10% w/w; and a lubricant in an amount of from about 0.01 to about 5% w/w, wherein presence of all components add to 100%.

Dexamethasone, or pregna-1,4-diene-3,20-dione, 9-fluoro-11,17,21-trihydroxy-16-methyl-, (11β,16α)- is represented by the following structure:

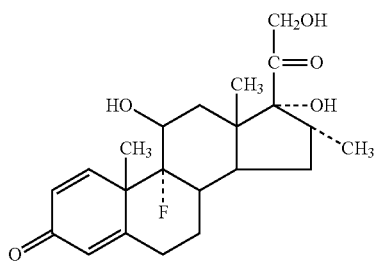

According to the principles provided herein, the pharmaceutical composition encompasses any pharmaceutically acceptable salt or solvate of dexamethasone. "Pharmaceutically acceptable salts" as used herein refer to any salt that is pharmaceutically acceptable and has the desired pharmacological properties. Such salts are, for example, inorganic or organic base addition salts, or inorganic or organic acid addition salts. Each possibility represents a separate embodiment.

Suitable pharmaceutically acceptable base addition salts include, but are not limited to, metallic salts of calcium, lithium, magnesium, potassium, sodium, aluminum and zinc; ammonium salts derived from ammonia, primary, secondary, tertiary and quaternary amines, non-limiting examples of which are trimethylamine, cyclohexylamine, benzylamine, dibenzylamine, 2-hydroxyethylamine, bis(2-hydroxyethyl)amine, phenylethylbenzylamine, dibenzylethylenediamine, procaine, chloroprocaine, quinine, choline, and N-methylglucosamine. Each possibility represents a separate embodiment. Salts with amino acids such as glycine, ornithine, histidine, phenylglycine, lysine, and arginine are contemplated as well. Each possibility represents a separate embodiment.

Pharmaceutically acceptable acid addition salts include, but are not limited to, those derived from inorganic acids such as hydrochloric, nitric, phosphoric, sulfuric, hydrobromic, hydriodic, and the like, as well as those derived from organic acids such as aliphatic mono- and dicarboxylic acids, phenyl-substituted alkanoic acids, hydroxy alkanoic acids, alkanedioic acids, aromatic acids, aliphatic and aromatic sulfonic acids and the like. Each possibility represents a separate embodiment. The salts thus include, but are not limited to, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Each possibility represents a separate embodiment. Salts with amino acids such as gluconate or galacturonate are contemplated as well. Each possibility represents a separate embodiment.

The acid addition salts and the base addition salts can be prepared by known methods of the art, for example by bringing the dexamethasone compound into contact with a sufficient amount of the desired acid or base to produce the salt.

Pharmaceutically acceptable salts of dexamethasone may comprise a counter-ion which contains one or more chiral centers so that different diastereomeric pairs or mixtures of such diastereomeric pairs of these salts are possible. It is to be understood that all the individual enantiomers, diastereomers and respective racemic and non-racemic mixtures thereof are within the scope of the disclosure. These mixtures of enantiomers and diastereomers can be separated into stereoisomerically uniform components in a known manner or synthesized a priori as separate enantiomers and diastereomers. Each possibility represents a separate embodiment.

The pharmaceutical composition of the disclosure may also contain a solvate of dexamethasone or salt thereof. The term "solvate" as used herein refers to a physical association of the compound with one or more solvent molecules. This physical association involves varying degrees of ionic and covalent bonding including, but not limited to, hydrogen bonding. In certain instances, the solvate will be capable of isolation. "Solvate" encompasses both solution-phase and isolatable solvates. Non-limiting examples of suitable solvates include ethanolates, methanolates and the like. Each possibility represents a separate embodiment. A "hydrate" is a solvate in which the solvent molecule is water.

It is contemplated that any polymorph of dexamethasone or pharmaceutically acceptable salt or solvate thereof may be present in the pharmaceutical composition of the disclosure. The term "polymorph" as used herein refers to a particular crystalline or amorphous state of a substance, which can be characterized by particular physical properties such as X-ray diffraction, electron diffraction, IR spectra, Raman spectra, melting point, and the like. Each possibility represents a separate embodiment.

Typically, the pharmaceutical composition disclosed herein contains dexamethasone in an amount of about 15% to about 25% of the total weight of the composition, including each integer within the specified range. In some embodiments, the pharmaceutical composition contains dexamethasone is in an amount of about 15%, about 16%, about 17%, about 18%, about 19%, about 20%, about 21%, about 22%, about 23%, about 24%, or about 25% of the total weight of the composition, with each possibility representing a separate embodiment. In one embodiment, the pharmaceutical composition contains dexamethasone in an amount of about 20% of the total weight of the composition.

According to the principles of the disclosure, the pharmaceutical composition comprising dexamethasone further comprises a solid carrier, which comprises at least one filler, at least one binder, at least one disintegrant, and at least one lubricant.

Suitable fillers include, but are not limited to, sugars such as lactose, glucose, fructose, or sucrose; microcrystalline cellulose; dicalcium phosphate; a sugar alcohol such as sorbitol, mannitol, maltitol, lactitol, xylitol, isomalt, and erythritol; and any combination thereof. Each possibility represents a separate embodiment. In one embodiment, the filler comprises lactose, preferably lactose monohydrate. In some embodiments, the filler is in an amount of about 45% to about 60% of the total weight of the composition, including each integer within the specified range. In other embodiments, the filler is in an amount of about 45%, about 46%, about 47%, about 48%, about 49%, about 50%, about 51%, about 52%, about 53%, about 54%, about 55%, about 56%, about 57%, about 58%, about 59%, or about 60% of the total weight of the composition, with each possibility representing a separate embodiment.

Suitable binders include, but are not limited to, polyvinylpyrrolidone (povidone; PVP), hydroxypropyl cellulose (HPC), hydroxypropyl methylcellulose (HPMC), starch, pregelatinized starch, sodium alginate, alginic acid, guar gum, acacia gum, xanthan gum, carbopol, carboxymethyl cellulose, ethyl cellulose, maltodextrin, vinylpyrrolidone and vinyl acetate copolymer, microcrystalline cellulose, and methyl cellulose, and any combination thereof. Each possibility represents a separate embodiment. In one embodiment, the binder comprises starch, polyvinylpyrrolidone, or a combination thereof. In some embodiments, the binder is in an amount of about 10% to about 30% of the total weight of the composition, including each integer within the specified range. In other embodiments, the binder is in an amount of about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% of the total weight of the composition, with each possibility representing a separate embodiment.

Suitable disintegrants include, but are not limited to, sodium carboxymethyl starch (sodium starch glycolate), low-substituted carboxymethyl cellulose sodium, cross-linked polyvinylpyrrolidone (crospovidone), cross-linked sodium carboxymethyl cellulose, pregelatinized starch (starch 1500), microcrystalline starch, water insoluble starch, calcium carboxymethyl cellulose, microcrystalline cellulose, low substituted hydroxypropyl cellulose, magnesium aluminum silicate, and any combination thereof. Each possibility represents a separate embodiment. In one embodiment, the disintegrant comprises sodium carboxymethyl starch (sodium starch glycolate). In some embodiments, the disintegrant is in an amount of about 2% to about 10% of the total weight of the composition, including each integer within the specified range. In another embodiment, the disintegrant is in an amount of about 4% to about 8% of the total weight of the composition, including each integer within the specified range. In yet another embodiment, the disintegrant is in an amount of about 2%, about 3%, about 4%, about 5%, about 6%, about 7%, about 8%, about 9%, or about 10% of the total weight of the composition, with each possibility representing a separate embodiment. It will be recognized by one of skill in the art that the disintegrant which is typically incorporated into the composition as part of the dry granulate, may also be incorporated into the composition as part of the extragranulate. In accordance with these embodiments, the disintegrant in the dry granulate and the disintegrant in the extragranulate may be the same or different, with each possibility representing a separate embodiment.

Suitable lubricants include, but are not limited to, magnesium stearate, calcium stearate, oleic acid, caprylic acid, stearic acid, magnesium isovalerate, calcium laurate, magnesium palmitate, behenic acid, glyceryl behenate, glyceryl stearate, sodium stearyl fumarate, potassium stearyl fumarate, zinc stearate, sodium oleate, sodium stearate, sodium benzoate, sodium acetate, sodium chloride, talc, solid polyethylene glycols, hydrogenated vegetable oil, and any combination thereof. Each possibility represents a separate embodiment. In one embodiment, the lubricant comprises magnesium stearate. In some embodiments, the lubricant is in an amount of about 0.01% to about 5% of the total weight of the composition, including each integer within the specified range. In another embodiment, the lubricant is in an amount of about 0.05% to about 3% of the total weight of the composition, including each integer within the specified range. In yet another embodiment, the lubricant is in an amount of about 0.01%, about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1%, about 1.5%, about 2%, about 2.5%, about 3%, about 3.5%, about 4%, about 4.5%, or about 5% of the total weight of the composition, with each possibility representing a separate embodiment.

According to certain aspects and embodiments, the pharmaceutical composition is in the form of a tablet, preferably uncoated. In accordance with these embodiments, there is provided an uncoated tablet comprising about 15 to about 25 wt.-% dexamethasone or a pharmaceutically acceptable salt or solvate thereof, about 45 to about 60 wt.-% filler, about 10 to about 30 wt.-% binder, about 2 to about 10 wt.-% disintegrant, and about 0.01 to about 5 wt.-% lubricant, wherein presence of all components add to 100 wt.-%.

Unexpectedly the uncoated tablets are capable of withstanding packaging, shipping, and consumer use without crumbling. In addition, uncoated tablets are cost-effective as they eliminate the need for additional coating step during manufacturing.

According to various aspects and embodiment, the pharmaceutical composition affords the immediate release of the active pharmaceutical ingredient, dexamethasone. The term "immediate release" as used herein refers to a composition which affords more than 70% release of the dexamethasone in 45 minutes, Apparatus 1 (basket), 50 rpm, 900 ml of dilute HCl (1 in 100) at 37° C.

The pharmaceutical composition disclosed herein can be prepared by any method known in the art. According to certain aspects and embodiments, there is provided a method of preparing a composition comprising high-load of dexamethasone, the method comprises wet granulating dexamethasone, a binder, a filler, and a disintegrant to obtain a wet granulate. The thus obtained wet granulate is subsequently dried to obtain a dry granulate. Finally, the dry granulate is admixed with a lubricant.

Wet granulation of dexamethasone, a binder, a filler, and a disintegrant can be performed using a mixer/granulator, such as a high-shear mixer/granulator. In one embodiment, the wet granulation is performed in a V-processor. In certain embodiments, wet granulation is performed by dry mixing dexamethasone with a binder, a filler, and a disintegrant to obtain a dry mixture, followed by spraying the dry mixture with a granulation solution or suspension to obtain a wet granulate. In one embodiment, the granulation solution or suspension comprises aqueous medium, i.e. water, optionally further comprising a binder to facilitate the formation of the granulate. In yet other embodiments, the granulation solution or suspension may comprise an organic medium, including, but not limited to, protic or aprotic solvents, optionally admixed with water, e.g. isopropyl alcohol and water, or acetone and water and the like. Each possibility represents a separate embodiment.

In certain embodiments, the step of drying the wet granulate is obtained by heating the granulate to a temperature above room temperature and maintaining the elevated temperature, typically for several hours until the Loss on Drying (LOD) % of the granulate reaches a desired value. The drying temperature, and thus the drying duration, can be varied in order to achieve the desired moisture content. According to the principles provided herein, the LOD % of the dry granulate is in the range of about 1.5% to about 5%, for example about 1.5%, about 2%, about 2.5%, about 3%, about 3.5%, about 4%, about 4.5%, or about 5%. Each possibility represents a separate embodiment. As used herein, "loss on drying" or "LOD" % can be measured by any of the many suitable means which are well known to those of skill in the art, including, but not limited to, Karl Fischer titration. Suitable measuring devices include, but not limited to, CENCO moisture balance, CSC digital moisture balance, Praxis moisture balance, HR-73 moisture analyzer (Mettler Toledo) etc.

Optionally, the dry granulate as well as each of the separate components of the composition is sieved and/or milled in order to reduce possible remaining lumps and to obtain a product with desired properties such as flowability, tapped density, and content uniformity. In one embodiment, sieving is performed as is known in the art, for example using vibrators or shakers.

In various aspects and embodiments, a second portion of a disintegrant which may be the same or different as the disintegrant in the dry granulate may optionally be added followed by the addition of a lubricant using any suitable type of mixer or blender. Non-limiting examples of mixers or blenders include simple paddle mixer, ribbon and/or tumbling mixers, plow blenders and drum agglomerators, V-blenders, double cone blenders, slant cone blenders, twin shell blenders, e.g., PATTERSON KELLEY V Blenders, GEMCO double cone blenders, diffusion blender and the like among others. Each possibility represents a separate embodiment.

In certain embodiments, the pharmaceutical composition disclosed herein is designed for oral administration. Typically, the composition is compressed to a tablet or a caplet. In accordance with these embodiments, the method of preparing the pharmaceutical composition may further comprise a step of compression. Suitable compression equipment includes, but is not limited to, mini press, single or double punch or rotary tablet press such as Killian, Korsch, Colton, Manesty, Stokes, Vector, and the like among others. Each possibility represents a separate embodiment. In some embodiments, the tablet or caplet is compressed using a compression force that affords a target hardness of about 30 N to about 150 N, including each integer within the specified range. Typical hardness values include, for example, about 40 N to about 130 N, preferably about 40 N to about 100 N, including each integer within the specified range. In various embodiments, the hardness or tablet breaking force is about 30 N, about 35 N, about 40 N, about 45 N, about 50 N, about 55 N, about 60 N, about 65 N, about 70 N, about 75 N, about 80 N, about 85 N, about 90 N, about 95 N, about 100 N, about 105 N, about 110 N, about 115 N, about 120 N, about 125 N, about 130 N, about 135 N, about 140 N, about 145 N, or about 150 N, with each possibility representing a separate embodiment. In certain embodiments, the tablet or caplet is further characterized by having friability of about 1% or less, for example about 0.01% to about 1%, preferably about 0.05% to about 0.5%. In various embodiments, the friability is 0.01%, about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, or about 1%, with each possibility representing a separate embodiment.

A plurality of tablets or caplets may be packed in a suitable package material, which advantageously protects them from light and moisture. Blisters or bottles made from aluminum and/or hard polymer (i.e. PVC/PE/PVDC or PVC/PVDC) are examples of such package materials.

The pharmaceutical composition disclosed herein is useful for the treatment of multiple myeloma in combination with at least one anti-cancer drug. In accordance with these embodiments, there is provided a method of treating multiple myeloma in a subject in need thereof, the method comprising administering to the subject a therapeutically effective amount of the pharmaceutical composition of the disclosure in combination with at least one anti-cancer drug. The subject in need thereof is primarily a mammal, preferably a human. The therapeutically effective amount of the pharmaceutical composition to be administered depends on various factors including, but not limited to, the subject being treated (age and gender) and the severity of the disease being treated, the products which are used in combination with, and can be determined by the judgment of the prescribing physician. Because of patient-to-patient variability, dosages are a guideline only and the physician may adjust doses of the compounds to achieve the level of effective treatment that the physician considers appropriate for the patient. In considering the degree of treatment desired, the physician must balance a variety of factors such as, but not limited to, the age of the patient and the presence of other diseases or conditions.

The term "therapeutically effective amount" as used herein refers to the amount that achieves the targeted biological activity following the administration of the desired dosage in a reasonable volume. The term "treating" as used herein refers to stopping or slowing down the progression of the disease. The term "treating" further includes the reduction in the occurrence of various symptoms associated with multiple myeloma which is a hematologic malignancy characterized by proliferation of neoplastic plasma cells in the bone marrow. Dexamethasone, which belongs to a group of medicines known as corticosteroids, reduces the activity of the immune system by attaching to receptors in various types of immune cells. In multiple myeloma, high-dose dexamethasone is used together with anti-cancer drug(s) to increase the efficacy of the chemotherapy. Furthermore, high-dose dexamethasone may reduce certain adverse events which are associated with chemotherapy, such as nausea and vomiting. Thus, in certain embodiments, the composition disclosed herein may be used to reduce the occurrence of any adverse events caused by the co-administered anti-cancer drug.

A suitable anti-cancer drug that may be co-administered with the pharmaceutical composition disclosed herein includes, but is not limited to, thalidomide. The term "co-administration" as used herein encompasses administration of the selected therapeutic agents to a single patient, and is intended to include treatment regimens in which the agents are not necessarily administered by the same route of administration or at the same time. It is contemplated that the co-administration of the composition of the disclosure and the anti-cancer drug is performed in a regimen which may be simultaneous, separate, or sequential. Each possibility represents a separate embodiment.

As used herein and in the appended claims, the term "about" refers to ±10%.

As used herein and in the appended claims, the singular forms "a", "an", and "the" include plural references unless the context clearly dictates otherwise. It should be noted that the term "and" or the term "or" are generally employed in its sense including "and/or" unless the context clearly dictates otherwise.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1

Compositions according to certain embodiments of the disclosure were prepared as follows:

Dry mixing of dexamethasone active ingredient with lactose monohydrate as a filler, a first portion of sodium carboxymethyl starch as a disintegrant, and corn starch as a binder was performed followed by wetting of the dry mixture with a granulation solution containing water and polyvinylpyrrolidone as a fluid binder to obtain a wet granulate. The granulate was then dried followed by sieving. A second portion of sodium carboxymethyl starch as a disintegrant was added followed by the addition of magnesium stearate as lubricant. Finally, the entire blend was subjected to compression.

Exemplary compositions within the scope of the present disclosure are outlined in Tables 1-7. The pharmaceutical compositions set forth in Tables 1-7 were evaluated for tablet thickness, hardness, and friability. The results are outlined in Table 8.

TABLE 1

| Substance | Mg/tablet |
| --- | --- |
| Dexamethasone | 20.0 |
| Lactose monohydrate | 58.0 |
| Sodium carboxymethyl starch | 6.0 |
| Corn starch | 12.5 |
| Polyvinylpyrrolidone | 2.5 |
| Magnesium stearate | 1.0 |
| Purified water | q.s. |
| Total | 100.0 |

TABLE 2

| Substance | Mg/tablet |
| --- | --- |
| Dexamethasone | 20.0 |
| Lactose monohydrate | 53.0 |
| Sodium carboxymethyl starch | 6.0 |
| Corn starch | 17.5 |
| Polyvinylpyrrolidone | 2.5 |
| Magnesium stearate | 1.0 |
| Purified water | q.s. |
| Total | 100.0 |

TABLE 3

| Substance | Mg/tablet |
| --- | --- |
| Dexamethasone | 20.0 |
| Lactose monohydrate | 48.0 |
| Sodium carboxymethyl starch | 6.0 |
| Corn starch | 22.5 |
| Polyvinylpyrrolidone | 2.5 |
| Magnesium stearate | 1.0 |
| Purified water | q.s. |
| Total | 100.0 |

TABLE 4

| Substance | Mg/tablet |
| --- | --- |
| Dexamethasone | 20.0 |
| Lactose monohydrate | 55.0 |
| Sodium carboxymethyl starch | 4.0 |
| Corn starch | 17.5 |
| Polyvinylpyrrolidone | 2.5 |
| Magnesium stearate | 1.0 |
| Purified water | q.s. |
| Total | 100.0 |

TABLE 5

| Substance | Mg/tablet |
| --- | --- |
| Dexamethasone | 20.0 |
| Lactose monohydrate | 51.0 |
| Sodium carboxymethyl starch | 8.0 |
| Corn starch | 17.5 |
| Polyvinylpyrrolidone | 2.5 |
| Magnesium stearate | 1.0 |
| Purified water | q.s. |
| Total | 100.0 |

TABLE 6

| Substance | Mg/tablet |
| --- | --- |
| Dexamethasone | 20.0 |
| Lactose monohydrate | 53.5 |
| Sodium carboxymethyl starch | 6.0 |
| Corn starch | 17.5 |
| Polyvinylpyrrolidone | 2.5 |
| Magnesium stearate | 0.5 |
| Purified water | q.s. |
| Total | 100.0 |

TABLE 7

| Substance | Mg/tablet |
| --- | --- |
| Dexamethasone | 20.0 |
| Lactose monohydrate | 52.5 |
| Sodium carboxymethyl starch | 6.0 |
| Corn starch | 17.5 |
| Polyvinylpyrrolidone | 2.5 |
| Magnesium stearate | 1.5 |
| Purified water | q.s. |
| Total | 100.0 |

TABLE 8

| Composition | Thickness [mm] | Hardness [N] | Friability [%] |
|---|---|---|---|
| Table 1 | 2.8 | 61 | 0.13 |
| Table 2 | 2.8 | 73 | 0.16 |
| Table 3 | 2.8 | 70 | 0.08 |
| Table 4 | 2.8 | 47 | 0.22 |
| Table 5 | 2.8 | 61 | 0.12 |
| Table 6 | 2.8 | 65 | 0.11 |
| Table 7 | 2.8 | 58 | 0.12 |

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A pharmaceutical composition comprising:
   i) about 15 to about 25 wt.-% dexamethasone or a pharmaceutically acceptable salt or solvate thereof;
   ii) about 45 to about 60 wt.-% filler;
   iii) about 10 to about 30 wt.-% binder;
   iv) about 2 to about 10 wt.-% disintegrant; and
   v) about 0.01 to about 5 wt.-% lubricant;
   wherein presence of all components add to 100 wt.-%, and wherein the pharmaceutical composition is prepared by wet granulation.

2. The pharmaceutical composition of claim 1, wherein the filler comprises lactose.

3. The pharmaceutical composition of claim 1, wherein the binder comprises starch, polyvinylpyrrolidone or a combination thereof.

4. The pharmaceutical composition of claim 1, wherein the disintegrant comprises sodium carboxymethyl starch.

5. The pharmaceutical composition of claim 1, wherein the lubricant comprises magnesium stearate.

6. The pharmaceutical composition of claim 1 in the form of a tablet.

7. The pharmaceutical composition of claim 6 in the form of an uncoated tablet.

8. The pharmaceutical composition of claim 1 formulated into a unit dosage form suitable for oral administration.

9. The pharmaceutical composition of claim 8, wherein the unit dosage form comprises 20 mg of dexamethasone.

10. A process for preparing the pharmaceutical composition of claim 1, the process comprising:
    i) wet granulating dexamethasone or a pharmaceutically acceptable salt or solvate thereof, a binder, a filler, and a disintegrant to obtain a wet granulate;
    ii) drying the wet granulate of step (i) to obtain a dry granulate having a Loss on Drying (LOD) % of about 1.5% to about 5%; and
    iii) admixing the dry granulate of step (ii) with a lubricant to obtain a pharmaceutical composition.

11. The process of claim 10, wherein step (i) comprises:
    $i_a$) dry mixing dexamethasone or a pharmaceutically acceptable salt or solvate thereof, a binder, a filler, and a disintegrant to obtain a dry mixture; and
    $i_b$) spraying the thus obtained dry mixture with a granulation solution or suspension to obtain a wet granulate.

12. The process of claim 10, further comprising the step of:
    iv) compressing the pharmaceutical composition of step iii) to obtain a tablet or a caplet.

13. A pharmaceutical composition prepared by the process of claim 10.

14. A method of treating multiple myeloma in a subject in need thereof comprising administering to the subject the pharmaceutical composition of claim 1 in combination with an anti-cancer drug.

15. The method of claim 14, wherein the anti-cancer drug is thalidomide.

16. An uncoated tablet comprising:
    i) about 15 to about 25 wt.-% dexamethasone or a pharmaceutically acceptable salt or solvate thereof;
    ii) about 45 to about 60 wt.-% filler;
    iii) about 10 to about 30 wt.-% binder;
    iv) about 2 to about 10 wt.-% disintegrant; and
    v) about 0.01 to about 5 wt.-% lubricant;
    wherein presence of all components add to 100 wt.-%, and wherein the uncoated tablet is prepared by wet granulation.

17. The uncoated tablet of claim 16, wherein the filler comprises lactose.

18. The uncoated tablet of claim 16, wherein the binder comprises starch, polyvinylpyrrolidone or a combination thereof.

19. The uncoated tablet of claim 16, wherein the disintegrant comprises sodium carboxymethyl starch.

20. The uncoated tablet of claim 16, wherein the lubricant comprises magnesium stearate.

21. The uncoated tablet of claim 16 comprising 20 mg of dexamethasone.

22. A process for preparing the uncoated tablet of claim 16, the process comprising:
    i) wet granulating dexamethasone or a pharmaceutically acceptable salt or solvate thereof, a binder, a filler, and a disintegrant to obtain a wet granulate;
    ii) drying the wet granulate of step (i) to obtain a dry granulate having a Loss on Drying (LOD) % of about 1.5% to about 5%;
    iii) admixing the dry granulate of step (ii) with a lubricant to obtain a pharmaceutical composition; and
    iv) compressing the pharmaceutical composition of step iii) to obtain an uncoated tablet.

23. The process of claim 22, wherein step (i) comprises:
    $i_a$) dry mixing dexamethasone or a pharmaceutically acceptable salt or solvate thereof, a binder, a filler, and a disintegrant to obtain a dry mixture; and
    $i_b$) spraying the thus obtained dry mixture with a granulation solution or suspension to obtain a wet granulate.

24. An uncoated tablet prepared by the process of claim 22.

25. A method of treating multiple myeloma in a subject in need thereof comprising administering to the subject the uncoated tablet of claim 16 in combination with an anti-cancer drug.

26. The method of claim 25, wherein the anti-cancer drug is thalidomide.

27. The pharmaceutical composition of claim 2, wherein the filler comprises lactose monohydrate.

28. The uncoated tablet of claim 17, wherein the filler comprises lactose monohydrate.

* * * * *